US005573525A

United States Patent [19]

Watson et al.

[11] Patent Number: 5,573,525

[45] Date of Patent: Nov. 12, 1996

[54] BOTTLE WITH CLOSURE ELEMENT FOR RECEIVING SYRINGE AND METHOD THEREFOR

[76] Inventors: Thomas L. Watson; Jaleh Shaban-Watson, both of 12318 Rue Fontainbleau, San Diego, Calif. 92131-2261

[21] Appl. No.: 388,135

[22] Filed: Feb. 13, 1995

Related U.S. Application Data

[62] Division of Ser. No. 174,874, Dec. 28, 1993, abandoned.

[51] Int. Cl.[6] .......... A61B 19/00

[52] U.S. Cl. .......... 604/403; 604/415; 215/306; 215/DIG. 3; 215/310; 220/375

[58] Field of Search .......... 604/403, 407, 604/905, 415; 215/307, 310, 329, 306, DIG. 3, 388, 389; 220/254, 709, 375; 128/DIG. 26

[56] References Cited

U.S. PATENT DOCUMENTS

| | | | |
|---|---|---|---|
| 1,219,937 | 3/1917 | Green | 604/403 |
| 2,815,879 | 12/1957 | Hermes . | |
| 4,230,112 | 10/1980 | Smith | 604/403 |
| 4,303,071 | 12/1981 | Smith | 604/403 |
| 5,364,387 | 11/1994 | Sweeny | 604/403 |
| 5,385,372 | 1/1995 | Utterberg | 215/306 |

*Primary Examiner*—John G. Weiss
*Assistant Examiner*—P. Zuttarelli
*Attorney, Agent, or Firm*—John L. Rogitz

[57] ABSTRACT

A medicine bottle is formed with a neck that defines an opening and a closed bottom opposite the opening. A closure element is engaged with the neck to block the opening, and the closure element is formed with a fluid passageway. A fitting is positioned in the fluid passageway. The fitting is configured for receiving the hub of a needleless syringe, and a tube which has a proximal end is positioned in the bottle with the proximal end in fluid communication with the fitting. The tube also has a distal end disposed near the bottom of the bottle. Consequently, the syringe can be engaged with the fitting for drawing liquid from the bottle into the syringe without inverting the bottom of the bottle over the neck of the bottle, even when the bottle is nearly empty.

5 Claims, 2 Drawing Sheets

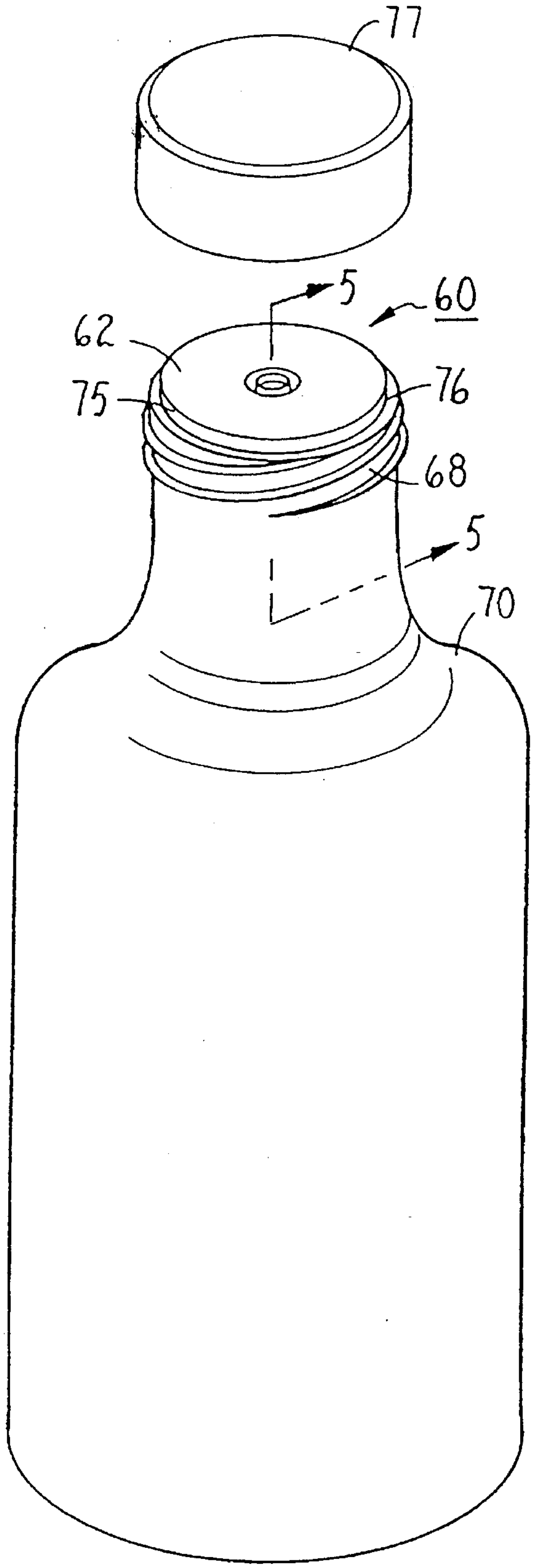
Fig. 4
Fig. 5
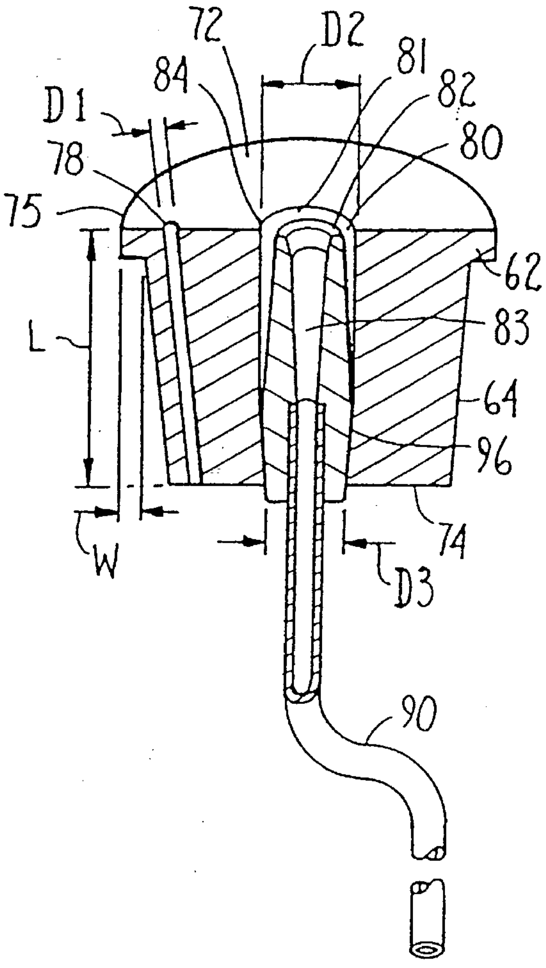

BOTTLE WITH CLOSURE ELEMENT FOR RECEIVING SYRINGE AND METHOD THEREFOR

This application is a divisional application of and claims priority from U.S. patent application Ser. No. 08/174,874 filed Dec. 28, 1993, now abandoned for an invention entitled "BOTTLE WITH CLOSURE ELEMENT FOR RECEIVING SYRINGE AND METHOD THEREFOR", in the name of the inventors of the present application."

FIELD OF THE INVENTION

The present invention relates generally to medicine dispensers, and more particularly to devices for extracting liquid medicine from container bottles.

BACKGROUND

Many liquid medicines for children and invalids are contained in, and must accordingly be dispensed from, container bottles. When dispensing the medicine from the bottle, it is frequently necessary to first draw medicine from the bottle into a syringe, to prepare a precise dosage for administration to the patient and to facilitate administering the medicine to the patient.

Administering liquid medicine with a syringe is often the optimal method of medicament administration for patients who have difficulty receiving medicine from, e.g., a spoon. Also, as stated above, a more precise dosage of liquid medicament can be administered with a syringe than with a spoon. For many liquid medicament therapies, administering a precise dosage is essential to success of the treatment.

Accordingly, needleless syringes have been provided for administering liquid medicament to patients. Typically, these syringes have a blunt-tipped hub which is advanced into the bottle. Then, the plunger of the syringe is manipulated to draw a precise amount of liquid through the hub into the syringe chamber. The syringe is next withdrawn from the bottle and used to administer the precise dosage of liquid medicament to the patient.

Unfortunately, in the case of many bottles, when the bottle is about one-third full, the liquid level falls below the hub of the syringe, even when the syringe is advanced as far as practicable into the bottle. Consequently, the bottle must be tipped to allow liquid to flow to the hub of the syringe. It can be appreciated that under these circumstances, liquid can easily spill out of the bottle, and it becomes difficult to draw the liquid medicament into the chamber of the syringe without also undesirably drawing air into the chamber. Further, it is cumbersome to tip the bottle while holding the syringe and simultaneously manipulating the plunger of the syringe to draw liquid into the chamber. Consequently, dispensing medicine from the bottle can be relatively time-consuming, particularly in view of the fact that the procedure noted above must ordinarily be performed repeatedly over the course of the therapy.

One example of an attempt to overcome some of the problems noted above is the device sold under the trade name "EZY Dose" by Apothecary Products Inc. of Minneapolis, Minn. The "EZY Dose" device includes a stopper with frusto-conical sides, for facilitating positioning the stopper into a variety of bottles in an interference fit with the neck of the bottle. The stopper is formed with a passageway, and a fitting is positioned at one end of the passageway for receiving the hub of a needleless syringe.

To dispense liquid from the bottle, the syringe is engaged with the fitting, the bottle is inverted, and the plunger of the syringe is manipulated to draw liquid into the syringe chamber. As can be appreciated from the disclosure above, however, one drawback of the "EZY Dose" device is that the bottle must be held in an inverted position while manipulating the plunger of the syringe. As stated above, this can be cumbersome.

Further, the end of the stopper on which the fitting is formed is not flush with the top edge of the bottle neck. Consequently, the cap of the bottle cannot be engaged with the bottle with the stopper positioned in the neck. Thus, the stopper must be positioned in the neck and then removed from the neck each time liquid medicament is to be dispensed from the bottle. Such repeated manipulation of the stopper is time-consuming.

As recognized by the present invention, a device can be provided for ameliorating the problems noted above. Accordingly, it is an object of the present invention to provide a device that can be engaged with a bottle and a syringe for facilitating drawing liquid from the bottle into the syringe. Another object of the present invention is to provide a liquid medicament dispensation device which is easy to use and cost-effective to manufacture.

SUMMARY OF THE INVENTION

A device is disclosed for receiving the hub of a needleless syringe to establish fluid communication between the syringe and a medicament bottle. The medicament bottle contains liquid medicament and is formed with a neck which defines an opening. The bottle also has a closed bottom that is distanced from the opening.

The device of the present invention includes a closure element formed with a passageway which extends through the closure element. As intended by the present invention, the closure element is engageable with the bottle to block the opening. A hollow fitting is positioned in the passageway and is configured for receiving the hub of the needleless syringe, and a tube has a proximal end in fluid communication with the hollow fitting and a distal end positionable adjacent the bottom of the bottle. With this combination of structure, the syringe can be engaged with the fitting for drawing liquid from the bottle into the syringe without inverting the bottom of the bottle over the neck of the bottle.

Preferably, the hollow fitting is made of elastic material and defines a fluid pathway. The fluid pathway of the fitting has a frusto-conical wall for guiding the hub of the syringe into close engagement with the fitting. In one intended embodiment, the neck of the bottle defines a proximal edge, and the closure element includes a cap threadably engageable with the bottle and a stopper that is formed with a proximal flange which is positioned against the proximal edge of the bottle. Accordingly, a fluid seal is established between the flange and bottle edge when the cap is engaged with the bottle.

In accordance with the present invention, the passageway of the stopper defines a wall, and the passageway includes a distal segment for closely receiving the fitting therein and a proximal segment. The wall of the proximal segment is distanced from the fitting to permit the fitting to expand when the hub of the syringe is engaged with the fitting. To prevent a vacuum from being established within the bottle when the syringe is manipulated, the stopper is formed with a vent passage that extends between the proximal and distal surfaces of the stopper.

In another intended embodiment, the closure element is a cap which is engageable with the bottle. In this embodiment, a plug can be provided for selectively blocking the fluid pathway of the fitting when the syringe is not engaged therewith.

In another aspect of the present invention, a liquid medicament dispensing apparatus includes a bottle which is formed with a neck, and the neck defines an opening. The bottle has a closed bottom opposite the opening, and the bottle defines a chamber for holding liquid. The apparatus further includes a needleless syringe formed with a hub, and a closure element which is positioned to block the opening, and the closure element is formed with a fluid passageway. Additionally, a conduit member includes a segment positioned in the fluid passageway of the closure element, and the conduit member includes a proximal end configured for closely receiving the hub of the syringe and a distal end disposed near the bottom of the bottle.

In still another aspect of the present invention, a device is disclosed for removing liquid from a bottle. The bottle is formed with a neck which defines an opening, and the bottle also has a bottom distanced from the opening when the bottle is oriented with the bottom below the neck. As intended by the present invention, the device includes a syringe formed with a hub and a closure element engaged with the bottle to block the opening, and the closure element is formed with a fluid passageway. A conduit member has a segment positioned in the fluid passageway of the closure element. The conduit member includes a proximal end configured for closely receiving the hub of the syringe, and a distal end disposed near the bottom of the bottle.

The details of the present invention, both as to its construction and operation, can best be understood in reference to the accompanying drawings, in which like numerals refer to like parts, and which:

BRIEF DESCRIPTION OF THE DRAWINGS

FIG. 4 is an exploded perspective view of an alternate embodiment of the bottle with closure element of the present invention; and FIG. 5 is a cross-sectional view as seen along the line 5—5 in FIG. 4, with the bottle removed for clarity.

DETAILED DESCRIPTION OF THE PREFERRED EMBODIMENT

Figure 1:
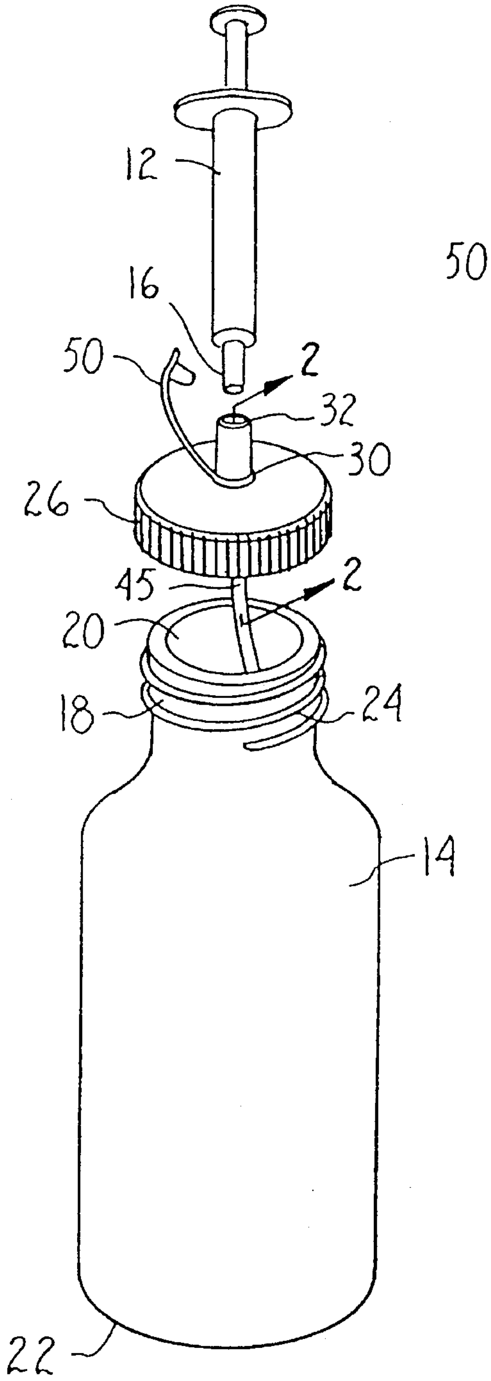
FIG. 1 is an exploded perspective view of the bottle with closure element of the present invention.

Referring initially to FIG. 1, a device is shown, generally designated 10, for interconnecting a needleless syringe 12 with a hollow standard medicine bottle 14. More specifically, the needleless syringe 12 is formed with a blunt hub 16, the bottle 14 is formed with a neck 18 which defines an opening 20, and the device 10 is positioned in the opening 20 for receiving the hub 16 of the syringe 12. FIG. 1 further shows that the bottle 14 has a bottom end 22 which is distanced from the opening 20, and the neck 18 is typically formed with a raised thread 24.

Figure 2:
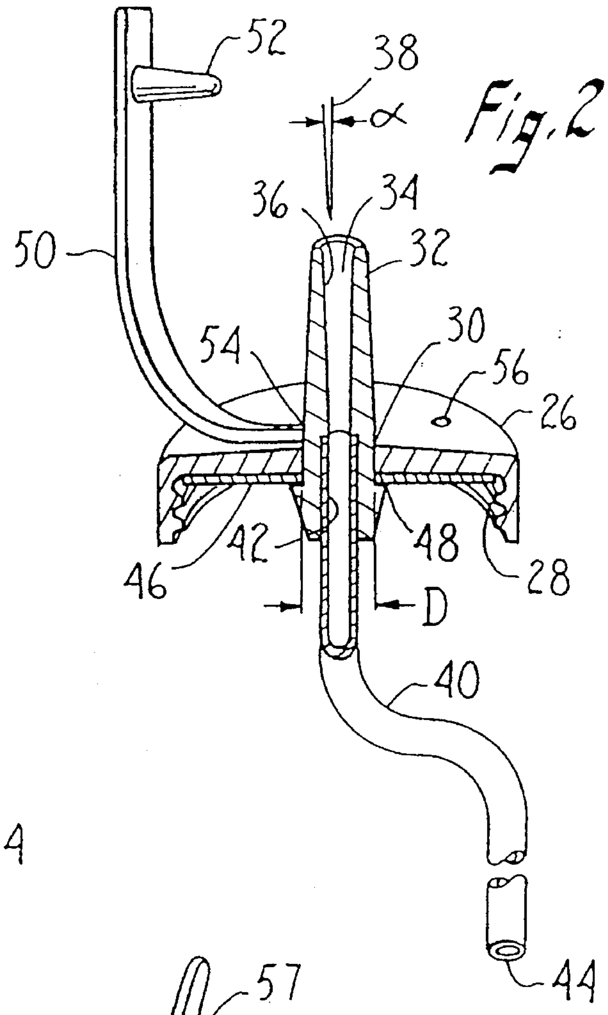
FIG. 2 is a cross-sectional view as seen along the line 2—2 in FIG. 1.

In cross reference to FIGS. 1 and 2, the device 10 includes a closure element 26. In the embodiment shown in FIGS. 1 and 2, the closure element 26 is a bottle cap configured for threadably engaging the neck 18 of bottle 14 to block the opening 20. More particularly, the closure element 26 is formed with threads 28 for engaging the threads 24 of the neck 18.

As shown in FIGS. 1 and 2, the closure element 26 is formed with a fluid passageway 30, and a fitting 32 is positioned in the fluid passageway 30. Preferably, the diameter "D" of the fluid passageway 30 is about two hundred sixty five thousandths of an inch (0.265"). Accordingly, to establish a tight interference fit with the fluid passageway 30, the diameter of the fitting 32 is slightly larger than the diameter "D" of the fluid passageway 30.

In one presently preferred embodiment, the fitting 32 is a standard eight French pediatric feeding tube. Accordingly, the fitting 32 defines a fluid pathway 34, and the fluid pathway 34 has a frusto-conical wall 36. As the skilled artisan will appreciate, the frusto-conical wall 36 is configured for guiding the hub 16 of the syringe 12 into the fluid pathway 34.

As shown in FIG. 2, an angle $\alpha$ is established between the wall 36 and the longitudinal axis 38 of the device 10. In the presently preferred embodiment, the angle $\alpha$ is between about one degree and about twenty five degrees (1°–25°), and is preferably about ten degrees (10°). It is to be understood that the fitting 32 is made of a slightly elastic material which can expand when the hub 16 of the syringe 12 is advanced into the fluid pathway 34 of the fitting 32.

FIGS. 1 and 2 also show that a tube 40 has a proximal segment 42, and the proximal segment 42 is disposed in fluid communication with the fluid pathway 34 of the fitting 32. If desired, the proximal end 42 of the tube 40 can be bonded to the fitting 32. Together, the tube 40 and fitting 32 establish a conduit member.

Further, a distal end 44 of the tube 40 is positioned adjacent the bottom 22 of the bottle 14. Preferably, the distal end 44 of the tube 40 rests on or near the bottom 22 of the bottle 14. As shown, the distal end is beveled (i.e. distal end 44 of the tube 40 lies in a plane which is not perpendicular to the longitudinal axis of the tube 40) to prevent the establishment of a seal between the bottom 22 of the bottle 14 and the distal end 44. With the above-disclosed combination of structure, the syringe 12 can be engaged with the fitting 32 for drawing liquid from the bottle 14 into the syringe 12 without inverting the bottom 22 of the bottle 14 over the neck 18 of the bottle 14.

FIG. 2 additionally shows that the closure element 26 includes a resilient annual washer 46. The fitting 32 is formed with a flange 48 and the flange 48 abuts the washer 46. With this combination of structure, the fitting 32 is held securely onto the closure element 26.

In addition, FIGS. 1 and 2 show that a plug 50 is provided which has a plug end 52. As shown, the plug end 52 is configured for selectively engaging the fluid pathway 34 of the fitting 32 in a close engagement fit therewith, to block the fluid pathway 34 when the syringe 12 is not engaged with the bottle 14. Also, the plug 50 is formed with an engagement end 54, and the engagement end 54 can be attached as shown to the fitting 32 or to the closure element 26 to thereby secure the plug 50. A vent orifice 56 can be formed through the closure element 26 if desired to prevent a vacuum from being established within the bottle 14 when the syringe 12 is manipulated to draw liquid into the syringe 12 from the bottle 14.

Figure 3:
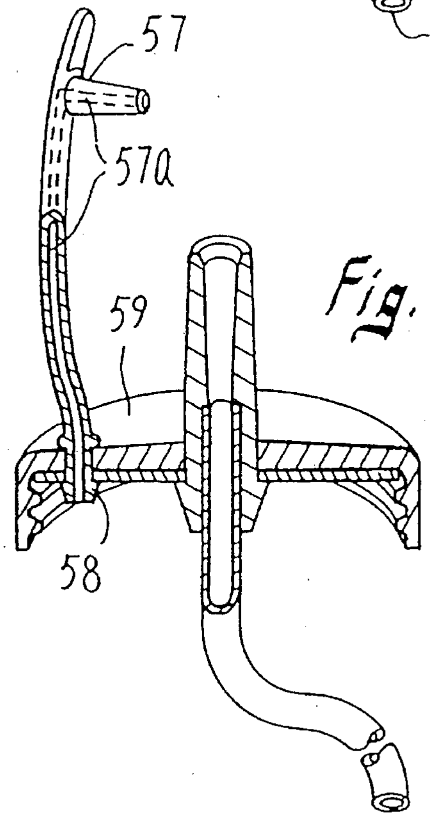
FIG. 3 is an exploded perspective view of an alternate embodiment of the bottle with closure element of the present invention, with portions of the vent passage shown in phantom.

Alternatively, referring briefly to FIG. 3, a plug 57 can have an engagement end 58 which extends through a cap 59. As shown, the plug 57 can be formed with a vent passage 57*a* to prevent a vacuum from being established within the bottle (not shown) with which the plug 57 is associated. It is to be understood that the embodiment shown in FIG. 3 is in all other essential respects identical to the embodiment shown in FIGS. 1 and 2.

Now referring to FIGS. 4 and 5, an alternate embodiment of the device of the present invention is shown, generally designated 60. As shown, the device 60 includes a resilient, preferably rubber, stopper 62. The stopper 62 has frusto-conical walls 64 that are configured for engaging in an interference fit an opening which is formed by a neck 68 of a bottle 70.

As shown best in FIG. 5, the stopper 62 has a proximal surface 72 and a distal surface 74, and the length "L" between the proximal surface 72 and distal surface 74 is about twenty two millimeters (22 mm). Also, the stopper 62 is formed with a proximal flange 75 which has a width "W" of about sixty three-thousandths of an inch (0.063").

As shown in FIG. 4, the neck 68 of the bottle 70 defines a proximal edge 76, and the proximal flange 75 of the stopper 62 is positioned against the proximal edge 76 of the neck 68. As shown, however, the flange 75 does not extend radially beyond the neck 68. Accordingly, when the stopper 62 is engaged with the neck 68 to block the opening, a child-resistant cap 77 can be engaged with the neck 68 of the bottle 70.

As a skilled artisan will recognize, the child-resistant cap 77 can be engaged with the neck 68 of the bottle 70 without having to remove the stopper 62 from the bottle 70. Also, the skilled artisan will recognize that when the cap 77 is engaged with the neck 68, the cap 77 urges against the flange 75 of the stopper 62 to establish a fluid seal between the flange 75 and the proximal edge 76 of the bottle 70. Further, the flange 75 prevents the stopper 62 from being accidentally pushed completely through the opening of the bottle 70 into the bottle 70. Additionally, the flange 75 establishes a convenient finger hold for removing the stopper 62 from the bottle 70.

A vent 78 is formed in the stopper 72 to prevent a vacuum lock in the bottle 70. Preferably, the diameter "D1" of the vent 78 is about forty six thousandths of an inch (0.046"). As shown in FIG. 5, the vent 78 extends from the top surface 72 to the bottom surface 74 of the stopper 62.

Still referring to FIG. 5, the stopper 62 is formed with a fluid passageway 80 that is defined by a wall 81. A fitting 82 which is in all essential respects identical to the fitting 32 shown in FIGS. 1 and 2 is positioned in the fluid passageway 80, and the fitting 82 defines a fluid pathway 83.

In the presently preferred embodiment, the diameter "D2" of a proximal segment 84 of the fluid passageway 80 is about four hundred six thousandths of an inch (0.406"). In contrast, the diameter "D3" of a distal segment 86 of the fluid passageway 80 is about one hundred seventy one thousandths of an inch (0.171"). Accordingly, the fitting 82 is closely received in the distal segment 86 of the fluid passageway 80, yet is distanced from the wall 81 of the proximal segment 84 of the passageway 80. Consequently, the fitting 82 can expand when the hub of the syringe (e.g. the syringe 12 shown in FIG. 1) is advanced into the fitting 82.

It is to be understood that while FIG. 5 shows that the fitting 82 and stopper 62 are made separately, the fitting 82 can be made integrally with the stopper 62, if desired. FIG. 5 also shows that a tube 90, which is in all substantial respects identical to the tube 40 shown in FIGS. 1 and 2, is engaged with the fitting 82 in fluid communication with the fluid pathway 83 of the fitting 82.

While the particular bottle with closure element as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. In a medicament bottle having liquid medicament therein, wherein the bottle is formed with a neck defining an opening and a closed bottom distanced therefrom, a device for receiving a hub of a needleless syringe, comprising:

a cap formed with a passageway therethrough, the cap being threadably engageable with the bottle to block the opening;

a hollow fitting positioned in the passageway and configured for receiving the hub of the needleless syringe;

a plug selectively engageable with the hollow fitting and formed with a plug end for blocking the hollow fitting and an engagement end attached to the cap; and a tube having a proximal end in fluid communication with the hollow fitting and a distal end positionable adjacent the bottom of the bottle, wherein the syringe can be engaged with the fitting for drawing liquid from the bottle into the syringe without inverting the bottom of the bottle over the neck of the bottle.

2. The device of claim 1, wherein the hollow fitting is made of elastic material and defines a fluid pathway therethrough, the fluid pathway having a frusto-conical wall for guiding the hub of the syringe into close engagement with the fitting.

3. A liquid medicament dispensing apparatus, comprising:

a bottle formed with a neck defining an opening and a closed bottom opposite the opening, the bottle defining a chamber for holding liquid;

a needleless syringe formed with a hub;

a cap threadably engageable with the neck of the bottle to block the opening, wherein the cap is formed with a fluid passageway;

a plug selectively engageable with the fluid passageway, the plug being formed with a plug end for blocking the fluid passageway and an engagement end attached to the cap; and a conduit member having a segment positioned in the fluid passageway of the cap, wherein the conduit member includes a proximal end configured for closely receiving the hub of the syringe and a distal end disposed near the bottom of the bottle.

4. The apparatus of claim 3, wherein the conduit member includes a hollow fitting for receiving the hub and a tube in fluid communication with the fitting.

5. The apparatus of claim 4, wherein the hollow fitting is made of elastic material and defines a fluid pathway therethrough, the fluid pathway having a frusto-conical wall for guiding the hub of the syringe into close engagement with the fitting.

* * * * *